(12) United States Patent
Greene, Jr. et al.

(10) Patent No.: US 6,500,190 B2
(45) Date of Patent: Dec. 31, 2002

(54) VASCULAR EMBOLIZATION WITH AN EXPANSIBLE IMPLANT

(75) Inventors: George R. Greene, Jr., Costa Mesa, CA (US); Robert F. Rosenbluth, Laguna Niguel, CA (US); Brian J. Cox, Laguna Niguel, CA (US)

(73) Assignee: MicroVention, Aliso Viejo, CA (US)

( * ) Notice: Subject to any disclaimer, the term of this patent is extended or adjusted under 35 U.S.C. 154(b) by 0 days.

(21) Appl. No.: 09/730,071

(22) Filed: Dec. 5, 2000

(65) Prior Publication Data

US 2001/0001835 A1 May 24, 2001

Related U.S. Application Data

(63) Continuation of application No. 09/110,816, filed on Jul. 6, 1998, now Pat. No. 6,165,193.

(51) Int. Cl.[7] .................................................. A61B 19/00
(52) U.S. Cl. ..................................... 606/191; 623/1.21
(58) Field of Search ........................ 606/191; 623/1.21, 623/1.11, 1.4, 1.39

(56) References Cited

U.S. PATENT DOCUMENTS

| | | | |
|---|---|---|---|
| 3,709,842 A | 1/1973 | Stoy et al. | 260/2.5 R |
| 4,365,621 A | 12/1982 | Brundin | 128/1 R |
| 4,436,684 A | 3/1984 | White | 264/138 |
| 4,506,393 A | 3/1985 | Murphy | 3/1 |
| 4,509,504 A | 4/1985 | Brundin | 128/1 R |
| 4,529,739 A | 7/1985 | Scott et al. | 521/72 |
| 4,551,132 A | 11/1985 | Pàsztor et al. | 604/52 |
| 4,663,358 A | 5/1987 | Hyon et al. | 521/64 |
| 4,795,741 A | 1/1989 | Leshchiner et al. | 514/21 |
| 4,819,637 A | 4/1989 | Dormandy, Jr. et al. | 128/325 |
| 4,873,707 A | 10/1989 | Robertson | 378/18 |
| 5,350,397 A | 9/1994 | Palermo et al. | 606/200 |

(List continued on next page.)

FOREIGN PATENT DOCUMENTS

| | | | |
|---|---|---|---|
| WO | 89/11257 | 11/1989 | A61F/2/28 |
| WO | 98/16266 | 4/1998 | A61L/27/00 |
| WO | 97/26939 | 7/1998 | A61M/29/00 |
| WO | 99/23954 | 5/1999 | A61B/17/12 |
| WO | 99/56783 | 11/1999 | A61K/47/30 |

OTHER PUBLICATIONS

Chirila, T.V. et al., "Poly(2–hydroxyethyl methacrylate) sponges as implant materials: in vivo and in vitro evaluation of cellular invasion," *Biomaterials*, 1993, vol. 14 No. 1.

(List continued on next page.)

*Primary Examiner*—David H. Willse
*Assistant Examiner*—Suzette J. Jackson
(74) *Attorney, Agent, or Firm*—Klein, O'Neill & Singh, LLP

(57) ABSTRACT

A vascular implant formed of a compressible foam material has a compressed configuration from which it is expansible into a configuration substantially conforming to the shape and size of a vascular site to be embodied. Preferably, the implant is formed of a hydrophobic, macro porous foam material, having an initial configuration of a scaled-down model of the vascular site, from which it is compressible into the compressed configuration. The implant is made by scanning the vascular site to create a digitized scan data set; using the scan data set to create a three-dimensional digitized virtual model of the vascular site; using the virtual model to create a scaled-down physical mold of the vascular site; and using the mold to create a vascular implant in the form of a scaled-down model of the vascular site. To embolism a vascular site, the implant is compressed and passed through a micro catheter, the distal end of which has been passed into a vascular site. Upon entering the vascular site, the implant expands in situ substantially to fill the vascular site. A retention element is contained within the micro catheter and has a distal end detachably connected to the implant. A flexible, tubular deployment element is used to pass the implant and the retention element through the micro catheter, and then to separate the implant from the retention element when the implant has been passed out of the micro catheter and into the vascular site.

5 Claims, 3 Drawing Sheets

U.S. PATENT DOCUMENTS

| | | | |
|---|---|---|---|
| 5,354,290 A | 10/1994 | Gross | 604/367 |
| 5,360,446 A | 11/1994 | Kennedy | 623/16 |
| 5,365,996 A | 11/1994 | Crook | 164/45 |
| 5,382,259 A | 1/1995 | Phelps et al. | 606/151 |
| 5,382,260 A | 1/1995 | Dormandy, Jr. et al. | 606/151 |
| 5,448,489 A | 9/1995 | Reuben | 364/474.05 |
| 5,452,407 A | 9/1995 | Crook | 395/121 |
| 5,456,693 A | 10/1995 | Conston et al. | 606/192 |
| 5,476,472 A | 12/1995 | Dormandy, Jr. et al. | 606/151 |
| 5,525,334 A | 6/1996 | Ito et al. | 424/78.35 |
| 5,541,234 A | 7/1996 | Unger et al. | 521/66 |
| 5,573,994 A | 11/1996 | Kabra et al. | 502/402 |
| 5,578,074 A | 11/1996 | Mirigian | 623/1 |
| 5,580,568 A | 12/1996 | Greff et al. | 424/423 |
| 5,582,619 A | 12/1996 | Ken | 606/191 |
| 5,624,461 A | 4/1997 | Mariant | 606/191 |
| 5,624,685 A | 4/1997 | Takahashi et al. | 424/488 |
| 5,645,558 A | 7/1997 | Horton | 606/191 |
| 5,658,308 A | 8/1997 | Snyder | 606/191 |
| 5,672,634 A | 9/1997 | Tseng et al. | 521/53 |
| 5,718,711 A | 2/1998 | Berenstein et al. | 606/191 |
| 5,738,667 A | 4/1998 | Solar | 604/280 |
| 5,750,585 A | 5/1998 | Park et al. | 521/143 |
| 5,752,974 A | 5/1998 | Rhee et al. | 606/214 |
| 5,762,125 A | 6/1998 | Mastrorio | 164/4.1 |
| 5,823,198 A * | 10/1998 | Jones et al. | 128/898 |
| 5,826,587 A | 10/1998 | Berenstein et al. | 128/898 |
| 5,911,731 A | 6/1999 | Pham et al. | 606/191 |
| 5,935,148 A | 8/1999 | Villar et al. | 606/213 |
| 5,957,948 A | 9/1999 | Mariant | 606/191 |
| 6,066,325 A | 5/2000 | Wallace et al. | 424/400 |
| 6,165,193 A * | 12/2000 | Green, Jr. et al. | 606/191 |
| 6,299,619 B1 * | 10/2001 | Green, Jr. et al. | 606/108 |
| 6,312,421 B1 | 11/2001 | Boock | |

OTHER PUBLICATIONS

Horàk, D. et al., "Hydrogels in endovascular embolization.II, Clinical use of spherical particles," *Biomaterials* (1986), vol. 7, Nov., pp. 467–470.

Horàk, D. et al., "New radiopaque polyHEMA–based hydrogel particles," *Journal of Biomedical Materials Research*, vol. 34, pp. 183–188, (1997).

Latchaw, R.E., M.D. et al.., "Polyvinyl Foam Embolization of Vascular and Neoplastic Lesions of the Head, Neck, and Spine," *Department of Radiology, University of Minnesota Hospitals*, Radiology 131:669–679, Jun. 1979.

MacDonald, W. et al., "Designing An Implant by CT Scanning and Solid Modelling," *The Journal of Bone and Joint Surgery*, vol. 68–B No. 2, pp. 208–212, Mar. 1986.

Wake, M.C. et al. "Dynamics of Fibrovascular Tissue Ingrowth in Hydrogel Foams," Cell Transplantation, vol. 4, No. 3, pp. 275–279, Nov. 3, 1995.

Woerly, S. et al., "Intracerebral implantation of synthetic polymer/biopolymer matrix: a new perspective for brain repair," PubMed Query.

* cited by examiner

VASCULAR EMBOLIZATION WITH AN EXPANSIBLE IMPLANT

CROSS REFERENCE TO RELATED APPLICATION

This application is a Continuation of application Ser. No. 09/110,816 filed Jul. 6, 1998 now U.S. Pat. No. 6,165,193.

FEDERALLY SPONSORED RESEARCH OR DEVELOPMENT

Not applicable

BACKGROUND OF THE INVENTION

The present invention relates to the field of methods and devices for the embolization of vascular aneurysms and similar vascular abnormalities. More specifically, the present invention relates to (a) an expansible vascular implant that is inserted into a vascular site such as an aneurysm to create an embolism therein; (b) a method of making the expansible implant; and (c) a method and an apparatus for embolizing a vascular site using the implant.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene glycol copolymer dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Patents: U.S. Pat. No. 4,551,132—Pásztor et al.; U.S. Pat. No. 4,795,741—Leshchiner et al.; U.S. Pat. No. 5,525,334—Ito et al.; and U.S. Pat. No. 5,580,568—Greff et al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a micro catheter to the vascular site. Examples of microcoils are disclosed in the following U.S. patents: U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.

The microcoil approach has met with some success in treating small aneurysms with narrow necks, but the coil must be tightly packed into the aneurysm to avoid shifting that can lead to recanalization. Microcoils have been less successful in the treatment of larger aneurysms, especially those with relatively wide necks. A disadvantage of microcoils is that they are not easily retrievable; if a coil migrates out of the aneurysm, a second procedure to retrieve it and move it back into place is necessary. Furthermore, complete packing of an aneurysm using microcoils can be difficult to achieve in practice.

A specific type of microcoil that has achieved a measure of success is the Guglielmi Detachable Coil ("GDC"). The GDC employs a platinum wire coil fixed to a stainless steel guidewire by a solder connection. After the coil is placed inside an aneurysm, an electrical current is applied to the guidewire, which heats sufficiently to melt the solder junction, thereby detaching the coil from the guidewire. The application of the current also creates a positive electrical charge on the coil, which attracts negatively-charged blood cells, platelets, and fibrinogen, thereby increasing the thrombogenicity of the coil. Several coils of different diameters and lengths can be packed into an aneurysm until the aneurysm is completely filled. The coils thus create and hold a thrombus within the aneurysm, inhibiting its displacement and its fragmentation.

The advantages of the GDC procedure are the ability to withdraw and relocate the coil if it migrates from its desired location, and the enhanced ability to promote the formation of a stable thrombus within the aneurysm. Nevertheless, as in conventional microcoil techniques, the successful use of the GDC procedure has been substantially limited to small aneurysms with narrow necks.

Still another approach to the embolization of an abnormal vascular site is the injection into the site of a biocompatible hydrogel, such as poly (2-hydroxyethyl methacrylate) ("pHEMA" or "PHEMA"); or a polyvinyl alcohol foam ("PAF"). See, e.g., Horák et al., "Hydrogels in Endovascular Embolization. II. Clinical Use of Spherical Particles", *Biomaterials*, Vol. 7, pp. 467–470 (November, 1986); Rao et al., "Hydrolysed Microspheres from Cross-Linked Polymethyl Methacrylate", *J. Neuroradiol.*, Vol. 18, pp. 61–69 (1991); Latchaw et al., "Polyvinyl Foam Embolization of Vascular and Neoplastic Lesions of the Head, Neck, and Spine", *Radiology*, Vol. 131, pp. 669–679 (June, 1979). These materials are delivered as microparticles in a carrier fluid that is injected into the vascular site, a process that has proven difficult to control.

A further development has been the formulation of the hydrogel materials into a preformed implant or plug that is installed in the vascular site by means such as a micro catheter. See, e.g., U.S. Pat. No. 5,258,042—Mehta and U.S. Pat. No. 5,456,693—Conston et al. These types of plugs or implants are primarily designed for obstructing blood flow through a tubular vessel or the neck of an aneurysm, and they are not easily adapted for precise implantation within a sack-shaped vascular structure, such as an aneurysm, so as to fill substantially the entire volume of the structure.

There has thus been a long-felt, but as yet unsatisfied need for an aneurysm treatment device and method that can substantially fill aneurysms of a large range of sizes, configurations, and neck widths with a thrombogenic medium with a minimal risk of inadvertent aneurysm rupture or blood vessel wall damage. There has been a further need for such a method and device that also allow for the precise locational deployment of the medium, while also minimizing the potential for migration away from the target location. In addition, a method and device meeting these criteria should also be relatively easy to use in a clinical setting. Such ease of use, for example, should preferably include a provision for good visualization of the device during and after deployment in an aneurysm.

SUMMARY OF THE INVENTION

Broadly, a first aspect of the present invention is a device for occluding a vascular site, such as an aneurysm, comprising a conformal vascular implant, formed of an expansible material, that is compressible from an initial configuration for insertion into the vascular site by means such as a micro catheter while the implant is in a compressed configuration, and that is expansible in situ into an expanded configuration in which it substantially fills the vascular site, thereby to embolism the site, wherein the initial configuration of the implant is a scaled-down model of the vascular site.

In a preferred embodiment, the implant is made of a hydrophobic, macro porous, polymeric, hydrogel foam material, in particular a water-swellable foam matrix formed as a macro porous solid comprising a foam stabilizing agent and a polymer or copolymer of a free radical polymerizable hydrophobic olefin monomer cross-linked with up to about 10% by weight of a multiolefin-functional cross-linking agent. The material is modified, or contains additives, to make the implant visible by conventional imaging techniques.

Another aspect of the present invention is a method of manufacturing a vascular implant, comprising the steps of: (a) imaging a vascular site by scanning the vascular site to create a digitized scan data set; (b) using the scan data set to create a three-dimensional digitized virtual model of the vascular site; and (c) forming a vascular implant device in the form of a physical model of the vascular site, using the virtual model, the implant being formed of a compressible and expansible biocompatible foam material. In a specific embodiment, the forming step (c) comprises the substeps of: (c)(1) using the virtual model to create a scaled-down, three-dimensional physical mold of the vascular site; and (c)(2) using the mold to create a vascular implant in the form of a scaled-down physical model of the vascular site.

In the preferred embodiment of the method of manufacturing the implant, the imaging step is performed with a scanning technique such as computer tomography (commonly called "CT" or "CAT"), magnetic resonance imaging (MRI), magnetic resonance angiography (MRA), or ultrasound. Commercially-available software, typically packaged with and employed by the scanning apparatus, reconstructs the scan data set created by the imaging into the three-dimensional digitized model of the vascular site. The digitized model is then translated, by commercially available software, into a form that is useable in a commercially available CAD/CAM program to create the scaled-down physical mold by means of stereolithography. A suitable implant material, preferably a macro porous hydrogel foam material, is injected in a liquid or semiliquid state into the mold. Once solidified, the hydrogel foam material is removed from the mold as an implant in the form of a scaled-down physical model of the vascular site.

A third aspect of the present invention is a method for embolizing a vascular site, comprising the steps of: (a) passing a micro catheter intravascularly so that its distal end is in a vascular site; (b) providing a vascular implant in the form of a scaled-down physical model of the vascular site, the implant being formed of a compressible and expansible biocompatible foam material; (c) compressing the implant into a compressed configuration dimensioned to pass through a micro catheter; (d) passing the implant, while it is in its compressed configuration, through the micro catheter so that the implant emerges from the distal end of the micro catheter into the vascular site; and (e) expanding the implant in situ substantially to fill the vascular site.

The apparatus employed in the embolization method comprises an elongate, flexible deployment element dimensioned to fit axially within an intravascular micro catheter; a filamentous implant retention element disposed axially through the deployment element from its proximal end to its distal end; and an implant device removably attached to the distal end of the retention element.

The implant device, in its preferred embodiment, is formed of a moldable, hydrophilically expansible, biocompatible foam material that has an initial configuration in the form of a scaled-down physical model of the vascular site, that is compressible into a compressed configuration that fits within the micro catheter, and that is hydrophilically expansible into an expanded configuration in which it is dimensioned substantially to conform to and fill the vascular site. Alternatively, the implant device may be formed of a non-hydrophobic foam material having an initial configuration that is substantially the same size and shape as the vascular site, and that restores itself to its initial configuration after it is released from its compressed configuration.

The retention element is preferably a flexible wire having a distal end configured to releasably engage the implant device while the implant device is in its compressed configuration, thus to retain the implant device within the distal end of the micro catheter while the distal end of the micro catheter is inserted into the vascular site. The wire is movable axially with the deployment element in the distal direction to expose the implant from the distal end of the micro catheter, and is movable proximally with respect to the deployment element to urge the implant device against the distal end of the deployment element, thereby push the implant device off of the wire. Thus released into the vascular site, the implant device expands into an expanded configuration in which it substantially conforms to and fills the vascular site.

The present invention provides a number of significant advantages. Specifically, the present invention provides an effective vascular embolization implant that can be deployed within a vascular site with excellent locational control, and with a lower risk of vascular rupture, tissue damage, or migration than with prior art implant devices. Furthermore, the implant device, by being modelled on the actual vascular site in which it is to be implanted, effects a conformal fit within the site that promotes effective embolization, and yet its ability to be delivered to the site in a highly compressed configuration facilitates precise and highly controllable deployment with a micro catheter. In addition, the method of fabricating the implant device, by modeling it on each individual site, allows implant devices to be made that can effectively embolism vascular sites having a wide variety of sizes, configurations, and (in the particular case of aneurysms) neck widths. These and other advantages will be readily appreciated from the detailed description that follows.

DETAILED DESCRIPTION OF THE INVENTION

The Method of Manufacturing a Vascular Implant. A first aspect of the present invention is a method of manufacturing a vascular implant device. The steps of a preferred embodiment of the manufacturing method are shown as a sequence of descriptive boxes in the flow chart of FIG. 1.

Figure 1:
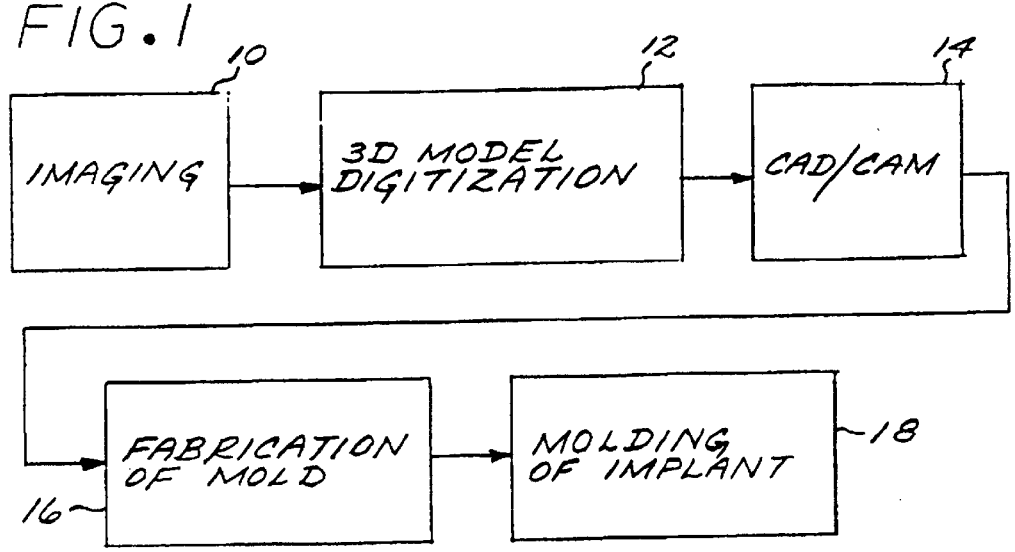
FIG. 1 is a flow chart showing a method of manufacturing a vascular implant in accordance with a preferred embodiment of the manufacturing method aspect of the present invention.

The first step, shown in box 10 of FIG. 1, is the step of creating an image of a vascular site, such as an aneurysm, in which an embolizing implant is to be installed. This imaging step is performed by scanning the site using any of several conventional imaging techniques, such as computer tomography, magnetic resonance imaging (MRI), magnetic resonance angiography (MRA), or ultrasound.

The result of the imaging step is a digitized scan data set that is stored in a computer memory, from which the data set is retrieved for operation of the next step: computerized reconstruction of a three-dimensional digitized virtual model of the vascular site (box 12 of FIG. 1). This step of creating a three-dimensional digital model is typically performed by software designed for this purpose that is packaged with and employed by the imaging apparatus.

The digitized, three-dimensional virtual model is then translated into a form in which it can be employed in a commercially-available CAD/CAM program (box 14) which controls a stereolithography process (box 16) to create a mold for forming an implant device. The translation of the virtual model is performed by software that is commercially available, for example, from Cyberform International, Inc., of Richardson, Tex., and from Stratasys, Inc., of Minneapolis, Minn. The mold (not shown) is preferably scaled-down from the dimensions of the vascular site, with a scale of about 1:2 to about 1:6, with about 1:4 being preferred. Alternatively, the mold may be made "life size" (i.e., 1:1); that is, a full-size or nearly full-size replica of the vascular site. The mold is used in the fabrication of a vascular implant device by conventional molding techniques (box 18).

Figure 2:
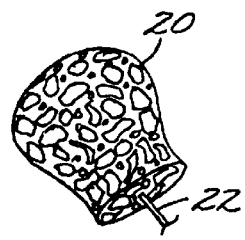
FIG. 2 is a perspective view of a vascular implant in accordance with a preferred embodiment of the vascular implant device aspect of the present invention, showing the implant in its initial configuration.

The Implant Device. A vascular implant device 20, in accordance with the present invention, is shown in FIG. 2 as it appears in its uncompressed or precompressed initial configuration after withdrawal from the mold. Preferably, the implant device 20 is molded directly onto the distal end portion of an elongate, flexible, filamentous retention element, such as a retention wire 22, for purposes to be described below. The retention wire 22 preferably has a distal end that terminates in a knob 24 (FIG. 5) for better retention of the implant device 20 thereon.

In the preferred embodiment, the implant device 20 is made of a biocompatible, macro porous, hydrophobic hydrogel foam material, in particular a water-swellable foam matrix formed as a macro porous solid comprising a foam stabilizing agent and a polymer or copolymer of a free radical polymerizable hydrophobic olefin monomer crosslinked with up to about 10% by weight of a multiolefinfunctional cross-linking agent. A suitable material of this type is described in U.S. Pat. No. 5,570,585—Park et al., the disclosure of which is incorporated herein by reference. Another suitable material is a porous hydrated polyvinyl alcohol foam (PAF) gel prepared from a polyvinyl alcohol solution in a mixed solvent consisting of water and a water-miscible organic solvent, as described, for example, in U.S. Pat. No. 4,663,358—Hyon et al., the disclosure of which is incorporated herein by reference. Still another suitable material is PHEMA, as discussed in the references cited above. See, e.g., Horák et al., supra, and Rao et al., supra. The foam material preferably has a void ratio of at least about 90%, and its hydrophobic properties are such that it has a water content of at least about 90% when fully hydrated.

Figure 4:
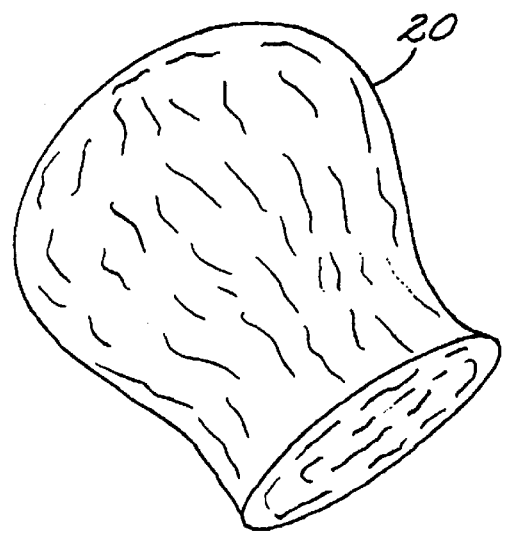
FIG. 4 is a perspective view of the implant of FIG. 2, showing the implant in its expanded configuration.

In a preferred embodiment, the implant device 20, in its initial, precompressed configuration, will have the same configuration as the vascular site, but it will be smaller, by a factor of approximately two to approximately six. The material of the implant device 20, and its initial size, are selected so that the implant device 20 is swellable or expansible to approximately the size of the vascular site, primarily by the hydrophobic absorption of water molecules from blood plasma, and secondarily by the filling of its pores with blood. The result is an expanded configuration for the implant device 20, as shown in FIG. 4, that is large enough substantially to fill the vascular site.

Alternatively, the implant 20 device can be molded so that in its initial, precompressed configuration, it is "life size", i.e., approximately the same size as the vascular site. In this case, the preferred material is a compressible, non-hydrophobic polymeric foam material, such as polyurethane. In actual clinical practice, a non-hydrophobic implant device 20 would advantageously be made slightly smaller than actual life size, to accommodate swelling due to the filling of the pores.

The foam material of the implant device 20, whether hydrophobic or non-hydrophobic, is advantageously modified, or contains additives, to make the implant 20 visible by conventional imaging techniques. For example, the foam can be impregnated with a water-insoluble radiopaque material such as barium sulfate, as described by Thanoo et al., "Radiopaque Hydrogel Microspheres", *J. Microencapsulation*, Vol. 6, No. 2, pp. 233–244 (1989). Alternatively, the hydrogel monomers can be copolymerized with radiopaque materials, as described in Horák et al., "New Radiopaque PolyHEMA-Based Hydrogel Particles", *J. Biomedical Materals Research*, Vol. 34, pp. 183–188 (1997).

Figure 3:
FIG. 3 is an elevational view of the implant of FIG. 2, showing the implant in its compressed configuration.

Whatever the material from which the implant device 20 is made, the implant device 20 must be compressible to a fraction of its initial size, preferably into a substantially cylindrical or lozenge-shaped configuration, as shown in FIG. 3. Compression of the implant device 20 can be performed by squeezing it or crimping it with any suitable fixture or implement (not shown), and then "setting" it in its compressed configuration by heating and/or drying, as is well-known. The purpose for this compression will be explained below in connection with the method of using the implant device 20 to embolism a vascular site.

Figure 5:
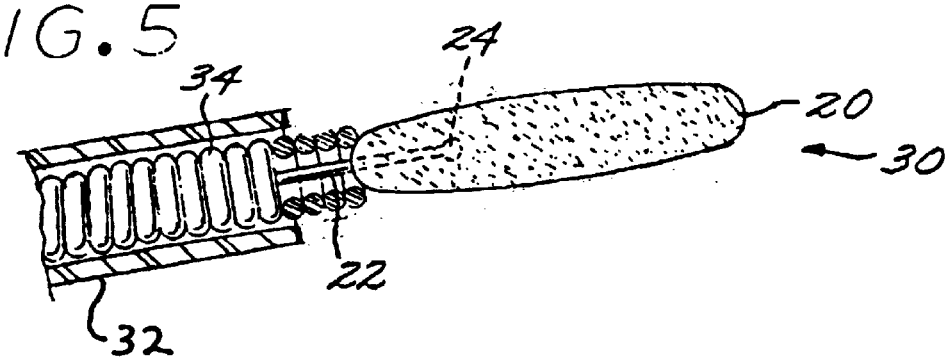
FIG. 5 is a cross-sectional view of an implanting apparatus employed in a method of embolizing a vascular site in accordance with a preferred embodiment of the embolizing method aspect of the present invention.

The Method and Apparatus for Embolizing a Vascular Site. The method of embolizing a vascular site using the implant device 20 is performed using an implanting apparatus 30, a preferred embodiment of which is shown in FIG. 5. The implanting apparatus 30 comprises the retention element or wire 22, a micro catheter 32, and an elongate, flexible, hollow, tubular element 34 (preferably a coil) that functions as an implant deployment element, as will be described below. With the implant device 20 attached to the distal end of the retention wire 22, the proximal end of the retention wire 22 is inserted into the distal end of the implant deployment element 34 and threaded axially through the implant deployment element 34 until the proximal end of the implant device 20 seats against, or is closely adjacent to, the distal end of the implant deployment element 34. The implant deployment element 34 is dimensioned for passing axially through the micro catheter 32. Thus, the implant deployment element 34, with the implant device 20 extending from its proximal end, may be inserted into the proximal end (not shown) of the micro catheter 32 and passed axially therethrough until the implant device 20 emerges from the distal end of the micro catheter 32, as shown in FIG. 5.

The implant device 20, in its compressed configuration, has a maximum outside diameter that is less than the inside diameter of the micro catheter 32, so that the implant device 20 can be passed through the micro catheter 32. The implant device 20 is preferably compressed and "set", as described above, before it is inserted into the micro catheter 32.

FIGS. 6 through 10 illustrate the steps employed in the method of embolizing a vascular site 40 using the implant device 20. The vascular site 40 shown in the drawings is a typical aneurysm, but the invention is not limited to any particular type of vascular site to be embodied.

Figure 6:
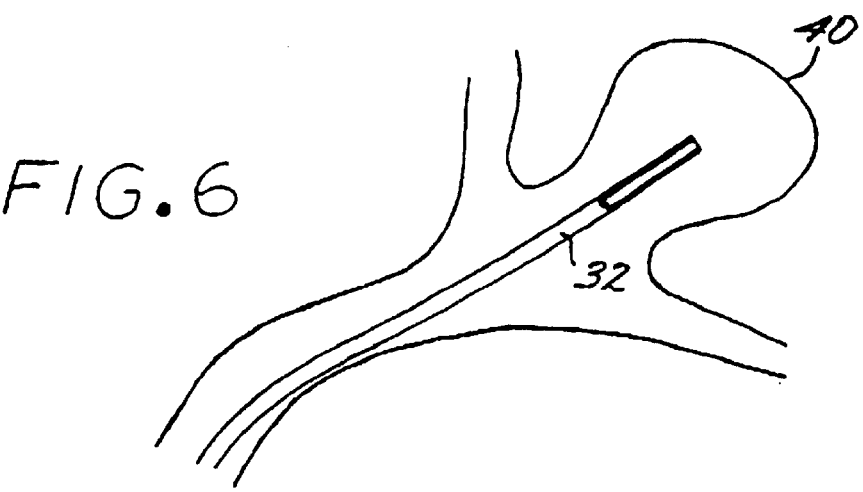
FIGS. 6 through 10 are semischematic views showing the steps in a method of embolizing a vascular site (specifically, an aneurysm) in accordance with a preferred embodiment of the embolizing method aspect of the present invention.

First, as shown in FIG. 6, the micro catheter 32 is threaded intravascularly, by conventional means, until its distal end is situated within the vascular site 40. This threading operation is typically performed by first introducing a catheter guidewire (not shown) along the desired micro catheter path, and then feeding the micro catheter 32 over the catheter guidewire until the micro catheter 32 is positioned substantially as shown in FIG. 6. The catheter guidewire is then removed.

Figure 7:
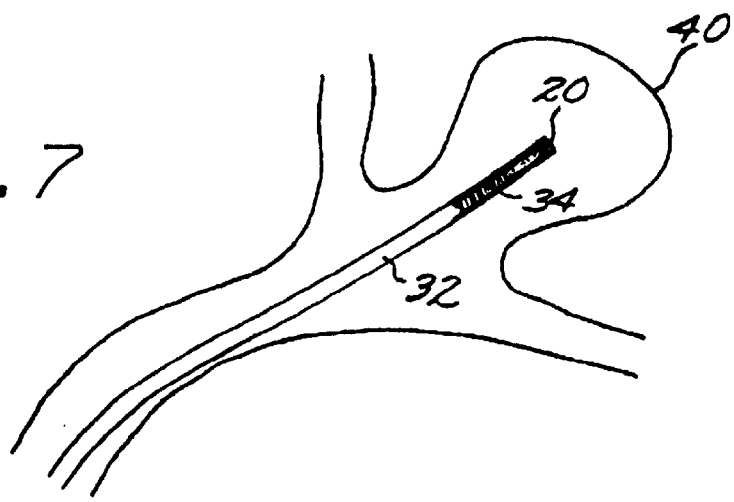
Figure 8:
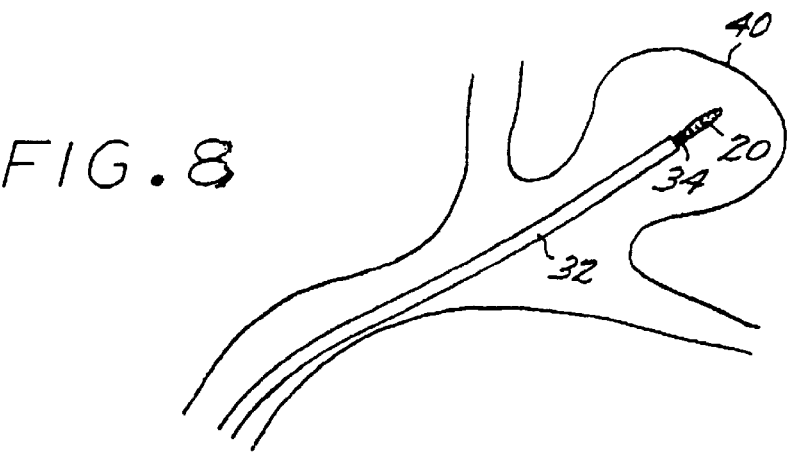
Figure 9:
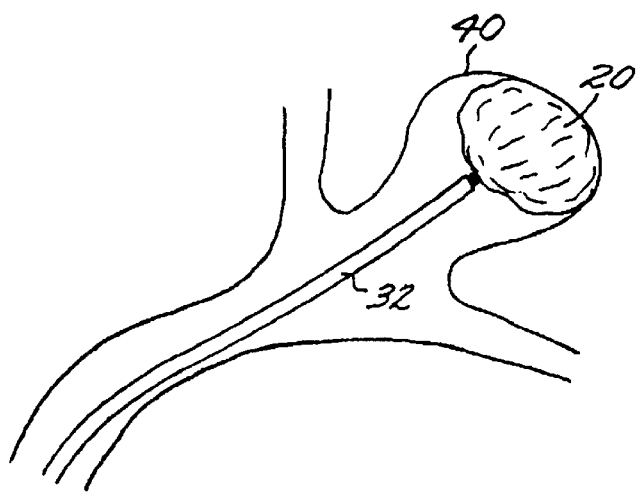

The implant deployment element 34, with the implant device 20 extending from its distal end, is then passed through the micro catheter 32, as described above, until the implant device 20 emerges from the distal end of the micro catheter 32 into the vascular site 40, as shown in FIGS. 7 and 8. When inserting the implant device 20 into the micro catheter 32, a biocompatible non-aqueous fluid, such as polyethylene glycol, may be injected into the micro catheter 32 to prevent premature expansion of the implant device 20 due to hydration, and to reduce friction with the interior of the micro catheter 32. The implant device 20 thus being exposed from the micro catheter 32 into the interior of the vascular site 40, the pores of the implant device 20 begin to absorb aqueous fluid from the blood within the vascular site 40 to release its "set", allowing it to begin assuming its expanded configuration, as shown in FIG. 9. Then, if the implant device 20 is of a hydrophobic material, it continues to expand due to hydrophobic hydration of the implant material, as well as from the filling of its pores with blood. If the implant device 20 is of a non-hydrophobic material, its expansion is due to the latter mechanism only.

Figure 10:
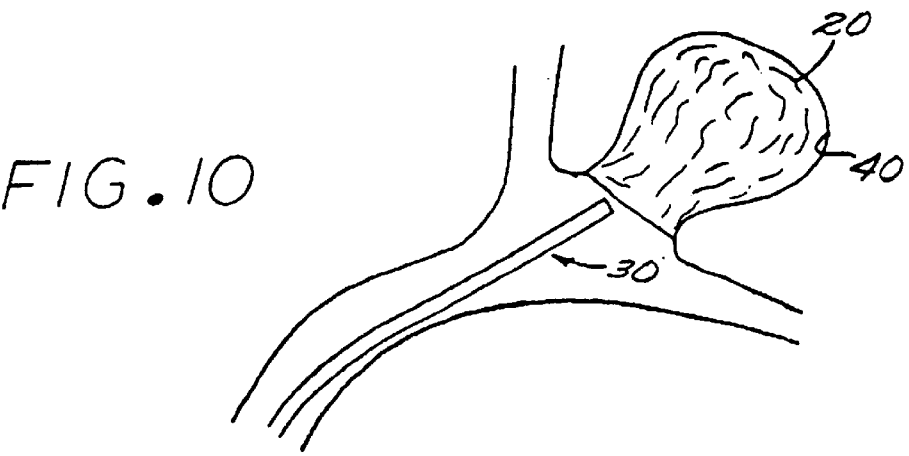

Finally, when the expansion of the implant device 20 is well underway (and not necessarily when it is completed), the retention wire 22 is pulled proximally with respect to the implant deployment element 34, causing the implant device to be pushed off the end of the installation wire 22 by means of the pressure applied to it by the distal end of the implant deployment element 34. The implant device 20, now free of the implanting apparatus 30, as shown in FIG. 10, may continue to expand until it substantially fills the vascular site 40. The implanting apparatus 30 is then removed, leaving the implant device 20 in place to embolism the vascular site 40.

While a preferred embodiment of the invention has been described above, a number of variations and modifications may suggest themselves to those skilled in the pertinent arts. For example, instead of custom-fabricating the implant device for each patient, implant devices in a variety of "standard" sizes and shapes may be made, and a particular implant device then selected for a patient based on the imaging of the vascular site. In this case, the fabrication method shown in FIG. 1 would be modified by first creating a three-dimensional digital model for each standardized implant, (box 12), and then proceeding with the subsequent steps shown in boxes 14, 16, and 18. Imaging (box 10) would be performed as an early step in the embolization procedure, followed by the selection of one of the standardized implant devices. This and other variations and modifications are considered within the spirit and scope of the invention, as described in the claims that follow.

What is claimed is:

1. A vascular implant device for embolizing a vascular site, the device being formed from a hydrophobic hydrogel material and having an initial configuration for the embolization of a vascular aneurysm from which it is expansible primarily by hydrophobic action into an expanded configuration.

2. The vascular implant device of claim 1, wherein the implant device is compressible into its initial configuration from its expanded configuration.

3. The vascular implant device of claim 1, wherein the device is radiopaque.

4. The vascular implant device of claim 1, wherein the device is expansible into an expanded configuration that substantially conforms to the size and shape of the vascular site.

5. The vascular implant device of claim 4, wherein the device is formed as a unitary molded element.

* * * * *

UNITED STATES PATENT AND TRADEMARK OFFICE
CERTIFICATE OF CORRECTION

PATENT NO. : 6,500,190 B2
DATED : December 31, 2002
INVENTOR(S) : Greene, Jr. et al.

It is certified that error appears in the above-identified patent and that said Letters Patent is hereby corrected as shown below:

Title page,
Item [56], U.S. PATENT DOCUMENTS, insert:

| | | | |
|---|---|---|---|
| -- 4,940,412 | 7/1990 | Blumenthal | 434/267 |
| 4,994,069 | 2/1991 | Richart, et al. | 606/191 |
| 5,007,936 | 4/1991 | Woolson | 623/23 |
| 5,133,731 | 7/1992 | Butler et al. | 606/191 |
| 5,156,777 | 10/1992 | Kaye | 264/40.1 |
| 5,184,306 | 2/1993 | Erdman et al. | 364/474.05 |
| 5,226,911 | 7/1993 | Chee et al. | 606/191 |
| 5,258,042 | 11/1993 | Mehta | 623/66 |
| 5,274,565 | 12/1993 | Reuben | 364/474.24 |
| 5,312,415 | 5/1994 | Palmero | 606/108 |
| 5,320,639 | 6/1994 | Rudnick | 606/213 --. |

OTHER PUBLICATIONS, insert:
-- McGurk, M. et al., "Rapid prototyping techniques for anatomical modeling in medicine," Ann R Coll Surg Engl, 1997; 79: 169-174.

McPherson, D.D. "Three-Dimensional Arterial Imaging," Scientific American: Science & Medicine, March/April 1996, pp. 22-31.

Rao, V.R.K., et al., "Hydrolysed Microshperes from Cross-linked Polymethyl Methacrylate (Hydrogel)," J. Neurodial., 1991, 18, 61-69.

Robertson, D.D. et al., "Design of Custom Hip Stem Prostheses Using Three-Dimensional Modeling," Journal of Computer Assisted Tomography, Vol. 11, No. 5, pp. 804-809, September/October 1987.

Thanoo, B.C. et al., "Radiopaque hydrogel microspheres," J. Microencapsulation 1989, Vol. 6, No. 2, pp. 233-244. --.

UNITED STATES PATENT AND TRADEMARK OFFICE
CERTIFICATE OF CORRECTION

PATENT NO.    : 6,500,190 B2
DATED          : December 31, 2002
INVENTOR(S)  : Greene, Jr. et al.

It is certified that error appears in the above-identified patent and that said Letters Patent is hereby corrected as shown below:

Item [57], ABSTRACT,
Line 5, "hydrophobic" should be -- hydrophilic --.
Line 15, "embolism" should be -- embolize --.

Column 3,
Line 47, "embolism" should be -- embolize --.
Lines 51 and 55, "hydrophobic" should be -- hydrophilic --.

Column 4,
Line 55, "hydrophobic" should be -- hydrophilic --.

Column 5,
Line 21, "embolism" should be -- embolize --.

Column 6,
Lines 33 and 37, "hydrophobic" should be -- hydrophilic --.
Line 40, "5,570,585" should be -- 5,750,585 --.
Lines 51 and 61, "hydrophobic" should be -- hydrophilic --.

Column 7,
Lines 3, 4 and 9, "hydrophobic" should be -- hydrophilic --.
Line 31, "embolism" should be -- embolize --.
Line 65, "embodied" should be -- embolized --.

Column 8,
Lines 24, 25 and 60, "hydrophobic" should be -- hydrophilic --.
Line 39, "embolism" should be -- embolize --.

UNITED STATES PATENT AND TRADEMARK OFFICE
CERTIFICATE OF CORRECTION

PATENT NO.    : 6,500,190 B2
DATED         : December 31, 2002
INVENTOR(S)   : Greene, Jr. et al.

It is certified that error appears in the above-identified patent and that said Letters Patent is hereby corrected as shown below:

<u>Column 8 cont'd,</u>
Lines 61-64, "configuration for the embolization of a vascular aneurysm from which it is expansible primarily by hydrophobic action into an expanded configuration." should be -- configuration from which it is expansible primarily by hydrophilic action into an expanded configuration for the embolization of a vascular aneurysm. --.

Signed and Sealed this

Eighteenth Day of February, 2003

JAMES E. ROGAN
*Director of the United States Patent and Trademark Office*